(12) United States Patent
Lee et al.

(10) Patent No.: US 7,719,689 B2
(45) Date of Patent: May 18, 2010

(54) AE/ULTRASOUND DETECTION SYSTEM, AND MATERIAL MONITORING APPARATUS AND NONDESTRUCTIVE INSPECTION APPARATUS EQUIPPED THE SYSTEM

(75) Inventors: Jung-Ryul Lee, Ibaraki (JP); Hiroshi Tsuda, Ibaraki (JP); Takahiro Arakawa, Yokohama (JP); Tomio Nakajima, Yokohama (JP)

(73) Assignees: National Institute of Advanced Industrial Science & Technology, Tokyo (JP); Ishikawajima Inspection & Instrumentation Co., Ltd, Tokyo (JP)

( * ) Notice: Subject to any disclaimer, the term of this patent is extended or adjusted under 35 U.S.C. 154(b) by 297 days.

(21) Appl. No.: 11/889,924

(22) Filed: Aug. 17, 2007

(65) Prior Publication Data

US 2008/0043243 A1 Feb. 21, 2008

(30) Foreign Application Priority Data

Aug. 18, 2006 (JP) ............................. 2006-223176

(51) Int. Cl.
G01B 9/02 (2006.01)
(52) U.S. Cl. ..................................................... 356/479
(58) Field of Classification Search ......... 356/477–480, 356/35.5, 519
See application file for complete search history.

(56) References Cited

U.S. PATENT DOCUMENTS 4,360,272 A * 11/1982 Schmadel et al. ........... 356/478
5,397,891 A * 3/1995 Udd et al. ............... 250/227.18
2008/0106745 A1* 5/2008 Haber et al. ................ 356/519

FOREIGN PATENT DOCUMENTS

| JP | 2003-169801 | 6/2003 |
|---|---|---|
| JP | 2005-009937 | 1/2005 |
| JP | 2005-326326 | 11/2005 |

* cited by examiner

Primary Examiner—Hwa S. A Lee
(74) Attorney, Agent, or Firm—Rader, Fishman & Grauer PLLC

(57) ABSTRACT

There is provided a system always capable of detecting AE/ultrasound received by an FBG, even when the FBG receives a change in temperature or strain and the Bragg wavelength is fluctuated. In the AE/ultrasound detection system, the reflected light from the FBG is caused to enter a Fabry-Perot filter having an FSR equal to or greater than the reflection wavelength band of the FBG. A change in the intensity of the transmitted light corresponds to the AE/ultrasound received by the FBG. Alternatively, the reflected light from FBG is caused to enter two Fabry-Perot filters having an FSR equal to or greater than the reflection wavelength band of the FBG and having the filter-transmittance peak wavelengths different from each other by FSR/4. The intensity of the transmitted light from each of the two Fabry-Perot filters is converted into a voltage signal, and the individual signals are subjected to addition and subtraction processes. Thus, a signal having a large amplitude corresponding to the AE/ultrasound received by the FBG can be obtained.

8 Claims, 10 Drawing Sheets

(a) DESIRABLE SHAPE OF REFLECTION (b) UNDESIRABLE SHAPE OF REFLECTION CHARACTERISTICS

DOTTED LINE REPRESENTS REFLECTION CHARACTERISTICS OF FBG
AND SOLID LINE REPRESENTS TRANSMISSION CHARACTERISTICS
OF FABRY-PEROT FILTER

REFLECTION WAVELENGTH BAND OF FBG > FSR OF FILTER

REFLECTION WAVELENGTH BAND OF FBG < FSR OF FILTER

REFLECTION WAVELENGTH BAND OF FBG = FSR OF FILTER

US 7,719,689 B2

AE/ULTRASOUND DETECTION SYSTEM, AND MATERIAL MONITORING APPARATUS AND NONDESTRUCTIVE INSPECTION APPARATUS EQUIPPED THE SYSTEM

BACKGROUND OF THE INVENTION

1. Field of the Invention

The present invention relates to an AE/ultrasound detection system. For example, it relates to a technique for detecting AE/ultrasound with the use of an FBG sensor, and to a system in which such technique is applied for evaluating the soundness of a structure.

2. Background Art

In recent years, for the purpose of improving the reliability of a structure, it has been expected to establish a soundness evaluation apparatus. When the soundness of a structure is evaluated, it is very important to measure strain and to detect defection such as cracking. Strain has been often measured with the use of a resistive strain gauge utilizing change in electrical resistance associated with deformation of metal. Further, as a method for detecting defection such as cracking, the detection of elastic-wave emission (AE: acoustic emission) associated with occurrence of defection and a nondestructive inspection utilizing ultrasound are conducted.

Piezoelectric elements have been widely used as AE detection sensors and ultrasound detection sensors in a nondestructive inspection using ultrasound. However, such AE/ultrasound measurement using piezoelectric elements involves the following problems. Namely, since piezoelectric elements are influenced by electromagnetic interference, the AE/ultrasound measurement cannot be conducted in the atmosphere of electromagnetic waves. Also, since piezoelectric elements have narrowband response frequency characteristics, it is necessary to change the kind of piezoelectric elements in accordance with the frequency band of the AE/ultrasound to be detected.

In recent years, in order to solve the above problems of the AE/ultrasound detection using piezoelectric elements, AE/ultrasound detection using an FBG (Fiber Bragg Grating) sensor, a kind of optical fiber sensor, (which will be occasionally referred to simply as an "FBG" hereafter in the specification) has drawn attention. Conventionally-proposed AE/ultrasound detection systems using the FBG are divided roughly into two kinds, depending on the light source used. One kind is a system using a laser light source, as disclosed in JP Patent Publication (Kokai) No. 2005-326326 A. In this system, laser light whose oscillation wavelength is set at a wavelength at which the reflectance of the FBG is decreased by half is caused to enter the FBG. Upon entry of the light, since the intensity of the light reflected from the FBG varies depending on the AE/ultrasound received by the FBG, the AE/ultrasound can be detected. The other type is a system using a broadband light source, as disclosed in JP Patent Publication (Kokai) No. 2005-009937 A. In this system, broadband light including a Bragg wavelength, the central reflection wavelength of the FBG, is caused to enter the FBG, and the reflected light is transmitted to an optical filter having the transmission wavelength band approximately equal to the reflection wavelength band of the FBG. At this point, a portion of the transmission wavelength region of the optical filter needs to overlap the reflection wavelength region of the FBG. By utilizing such phenomenon; that is, the transmitted-light intensity or the reflected-light intensity of the optical filter changes depending on the AE/ultrasound received by the FBG, the AE/ultrasound can be detected.

However, the Bragg wavelength of the FBG fluctuates depending on the temperature and strain received by the FBG. For example, in the case of a FBG having a Bragg wavelength of 1550 nm generally used for evaluating the soundness of a structure, the Bragg wavelength varies by 10 pm for a temperature of 1° C. with respect to the reflection wavelength band from 200 pm to 2000 pm, and the bragg wavelength also varies by 1.2 pm per micro strain. Thus, when the FBG receives a large change in temperature and strain, based on the system using a laser light source, there are cases in which the laser oscillation wavelength does not fall within the reflection wavelength region of the FBG. Similarly, based on the system using a broadband light source, there is a situation in which the transmission wavelength region of the optical filter does not cross the reflection wavelength region of the FBG. In such cases, the AE/ultrasound received by the FBG cannot be detected. Thus, it is necessary to control the laser oscillation wavelength or the optical-filter transmission wavelength in accordance with the fluctuation of the Bragg wavelength of the FBG. However, when the Bragg wavelength of the FBG fluctuates at high speed, such control cannot follow the change of the Bragg wavelength, and it is therefore conceivable that the AE/ultrasound cannot be detected. Particularly, since the AE generated upon destruction of a material is a phenomenon caused along with a large change of strain, a large fluctuation of the Bragg wavelength is caused upon occurrence of the AE. Thus, it is conceivable that the AE detection is very difficult with convention measurement systems.

In order to overcome the disadvantage, JP Patent Publication (Kokai) No. 2003-169801 A discloses a technique in which two thermally-coupled Bragg gratings made of the same material are used, so that the ultrasound received by the Bragg gratings can always be detected. In this technique, the Bragg gratings of the sensor and the filter that are thermally-coupled are synchronized upon receiving a temperature change, and the Bragg wavelengths are thus fluctuated.

SUMMARY OF THE INVENTION

However, based on the ultrasound detection disclosed in JP Patent Publication (Kokai) No. 2003-169801 A, when the sensor portion receives strain change, there may be a situation where ultrasound cannot be detected since the Bragg wavelengths of the sensor portion and the filter do not fluctuate in synchronization with each other.

The present invention has been made in view of such circumstances, and therefore it provides a system always capable of detecting the AE/ultrasound received by the FBG, even when the Bragg wavelength of the FBG is fluctuated upon receiving a change in temperature or strain.

In order to solve the above problems, in the AE/ultrasound detection system according to the present invention, reflected light from the FBG is caused to enter a Fabry-Perot filter having an FSR equal to or greater than the reflection wavelength band of the FBG. A change of the intensity of the transmitted light from the filter corresponds to the AE/ultrasound received by the FBG.

Further, in the AE/ultrasound detection system, the reflected light from the FBG is caused to enter two Fabry-Perot filters, each FSR thereof being equal to or greater than the reflection wavelength band of the FBG and the transmittance peak wavelengths thereof differ by FSR/4. The transmitted-light intensity of each of the two Fabry-Perot filters is converted into a voltage signal, and the individual signals are then subjected to addition and subtraction processes. In this way, a signal having a large amplitude corresponding to the AE/ultrasound received by the FBG can be obtained. A signal having the larger amplitude of the two signals subjected to the addition and subtraction processes corresponds to the AE/ultrasound received by the FBG.

It is preferable that an apodized FBG whose reflection characteristics exhibit no side lobes be used as the FBG. Further, for the detection of the AE/ultrasound, it is desirable to use an FBG whose reflection characteristics are not saturated; that is, an FBG that does not have a flat reflectance-wavelength relationship in the wavelength range in which the reflectance of the FBG reaches maximum. An FBG having a triangular reflectance-wavelength relationship is ideal for the detection of the AE/ultrasound.

Namely, the AE/ultrasound detection system according to the present invention comprises: a broadband light source for emitting broadband-wavelength light; an FBG sensor that is attached to an object-to-be-inspected and that the broadband-wavelength light enters; a filter having periodic transmission characteristics so as to transmit part of the reflected light or transmitted light from the FBG sensor; and photoelectric conversion means for converting the intensity of the transmitted light from the filter into an electric signal. Further, the broadband light source emits broadband light including the Bragg wavelength of the FBG, and the filter has an FSR equal to or greater than the reflection wavelength band or transmission wavelength band of the FBG. Furthermore, it is preferable that the transmittance peak wavelength of the filter be equal to a wavelength at which the reflectance or transmittance of the FBG is decreased by half.

Further, the AE/ultrasound detection system according to the present invention comprises: a broadband light source for emitting broadband-wavelength light; an FBG sensor that is attached to an object-to-be-inspected and that the broadband-wavelength light enters; light dividing means that divides reflected light or transmitted light from the FBG sensor so as to produce a first reflected light or transmitted light and a second reflected light or transmitted light; a first filter having periodic transmission characteristics so as to transmit part of the first reflected light or transmitted light; a second filter having periodic transmission characteristics and having its transmittance peak wavelength separated from that of the first filter by FSR/4 so as to transmit part of the second reflected light or transmitted light; and photoelectric conversion means for converting the intensity of the transmitted light from each of the first and second filters into an electric signal. The system further comprises processing means for performing addition and subtraction processes on the electric signal that is obtained by the conversion means and that corresponds to the intensity of the transmitted light from each of the filters. In the system, it is preferable that the broadband light source emit broadband light including the Bragg wavelength of the FBG and that the first and second filters have an FSR equal to or greater than the reflection wavelength band or transmission wavelength band of the FBG.

Preferably, in the AE/ultrasound detection system according to the present invention, the characteristics of the reflected light or transmitted light from the FBG sensor show those of an FBG on which an apodization process has been performed, thereby exhibiting no side lobes, and the characteristics are not saturated in a wavelength region in which the reflectance reaches maximum.

Further, in the above system, it is preferable that the filter be a Fabry-Perot filter or an AWG filter.

Still further, the material monitoring apparatus of the present invention comprises any one of the above AE/ultrasound detection systems, and it finds microscopic material destruction by detecting acoustic emission generated upon destruction of a material.

Furthermore, the nondestructive inspection apparatus of the present invention comprises any one of the above AE/ultrasound detection systems, and it conducts nondestructive inspection on a material or a structure with the use of ultrasound.

The present invention will be clarified hereafter in more detail by way of the description of preferred embodiments and the attached drawings.

EFFECTS OF THE INVENTION

In accordance with the present invention, AE/ultrasound can be detected with the use of an FBG sensor even in a situation where temperature/strain fluctuates at high speed, and therefore, a highly-reliable structure soundness evaluation system utilizing the AE/ultrasound can be provided.

BRIEF DESCRIPTION OF THE DRAWINGS

FIG. 5(a) shows the relationship where a filter-transmittance peak wavelength matches a wavelength at which the reflectance of the FBG is decreased by half; FIG. 5(b) shows the relationship where the Bragg wavelength of the FBG is located in the middle of adjacent filter-transmittance peak wavelengths; and FIG. 5(c) shows the relationship where the Bragg wavelength of the FBG matches the filter-transmittance peak wavelength.

FIG. 12(a) shows the positional relationship between the reflected-light intensity distribution of the FBG and the transmittance peak wavelengths of the two filters when the relative wavelength is −3FSR/8; and FIG. 12(b) shows the positional relationship between the reflected-light intensity distribution of the FBG and the transmittance peak wavelengths of the two filters when the relative wavelength is −FSR/8.

DESCRIPTION OF PREFERRED EMBODIMENTS OF THE INVENTION

Embodiments of the present invention will be described hereafter with reference to the attached drawings.

First Embodiment

Figure 1:
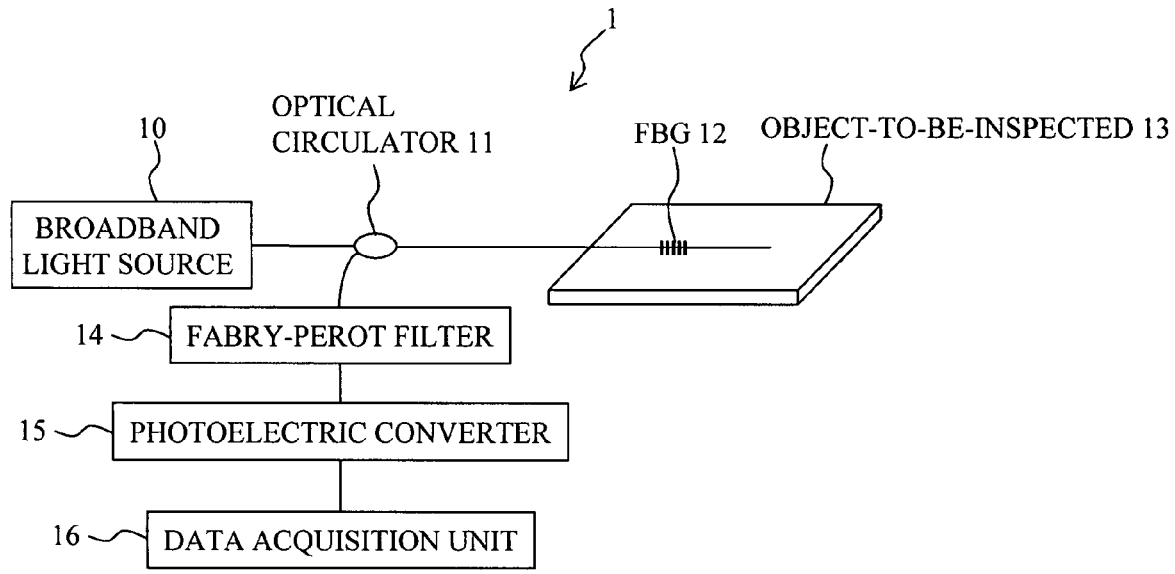
FIG. 1 schematically shows the structure of an AE/ultrasound detection system according to an embodiment of the present invention.

FIG. 1 shows a basic structure of an AE/ultrasound detection system according to a first embodiment of the present invention. An AE/ultrasound detection system 1 shown in FIG. 1 adopts a structure in which a broadband light source and one Fabry-Perot filter are combined.

As shown in FIG. 1, the AE/ultrasound detection system 1 is used for evaluating the soundness of an object-to-be-inspected 13, and it comprises: a broadband light source 10; an optical circulator 11; an FBG 12 (having been subjected to an apodization process); a Fabry-Perot filter 14; a photoelectric converter 15; and a data acquisition unit 16.

Referring to FIG. 1, broadband light from the broadband light source 10 enters the FBG 12 via the optical circulator 11. The FBG refers to a sensor having a diffraction grating structure in which the refraction index of the core portion of an optical fiber is periodically changed. When light enters the FBG, a wavelength component referred to as a Bragg wavelength is reflected by the FBG and the remaining components are allowed to pass therethrough. A shift amount of this Bragg wavelength changes depending on strain or temperature. Further, the FBG 12 has been previously subjected to an apodization process, and therefore, the distribution curve of the light reflected thereby exhibits a Gaussian distribution.

The reflected light from the FBG 12 enters the Fabry-Perot filter 14 via the optical circulator 11. The Fabry-Perot filter 14 does not transmit all the light incident thereon but it transmits only the light having a predetermined wavelength. Next, the transmitted light is inputted to the photoelectric converter 15, which converts the light into an electrical output corresponding to the light intensity. The data acquisition unit 16 causes a display unit not shown in the figure to display or a recording device not shown in the figure to record the electrical output, as the AE/ultrasound detected by the FBG 12.

Figure 2:
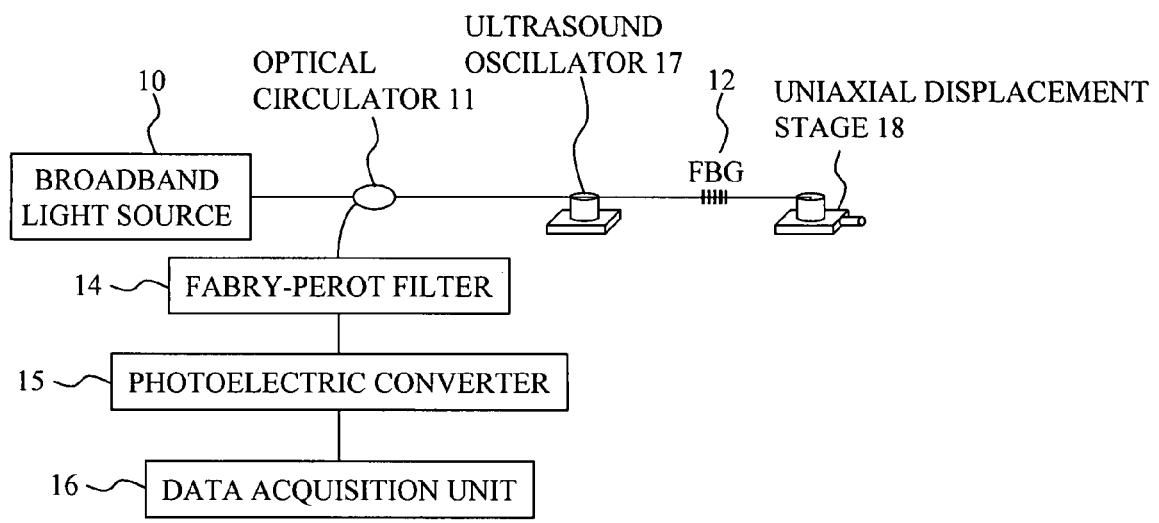
FIG. 2 schematically shows the structure of a system used in AE/ultrasound measurement experiment (1).

Next, an AE/ultrasound measurement experiment will be described so that the operation of the AE/ultrasound detection system 1 of the present embodiment will be understood more clearly. FIG. 2 shows a system for the experiment, and an ultrasound oscillator 17 and a uniaxial displacement stage 18 are provided in order to represent a pseudo strain placed on the object-to-be-inspected 13 when conducting the experiment. The other features are the same as those of FIG. 1.

Figure 3:
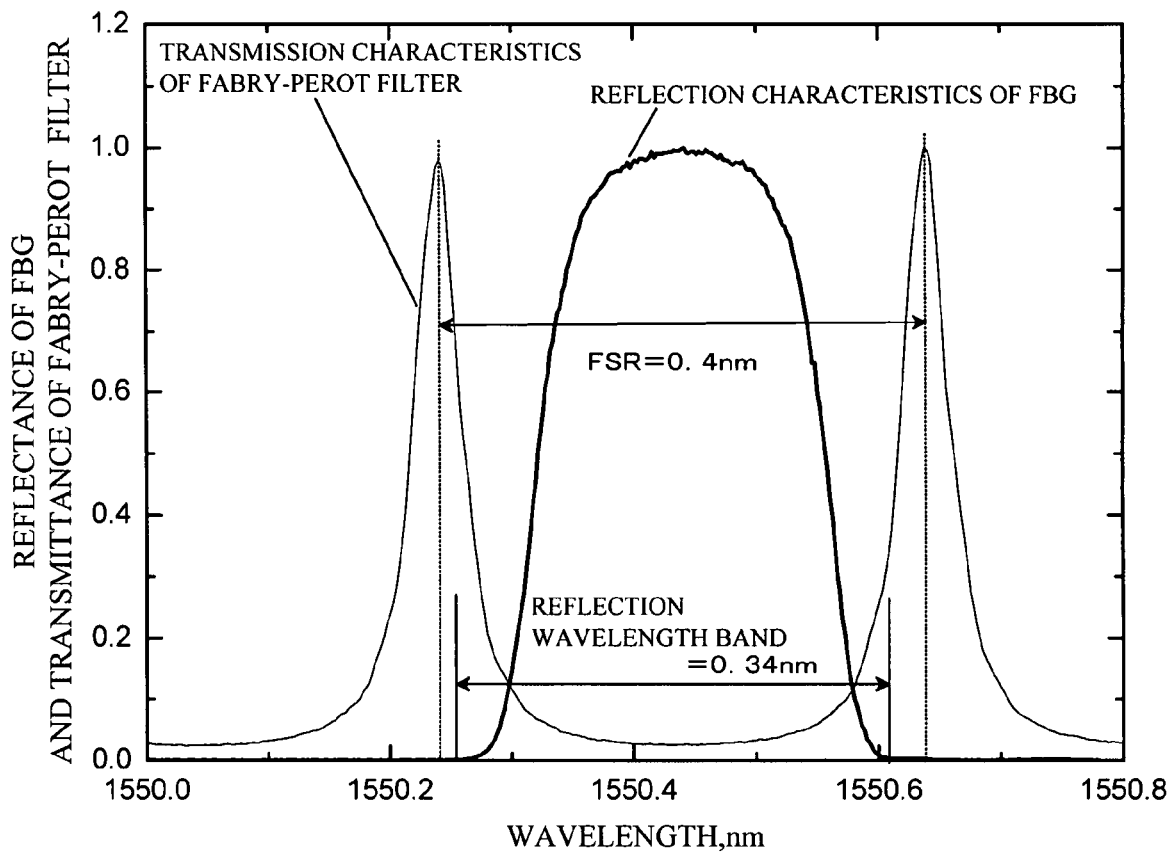
FIG. 3 shows optical characteristics of an FBG 12 and a Fabry-Perot filter.
Figure 4:
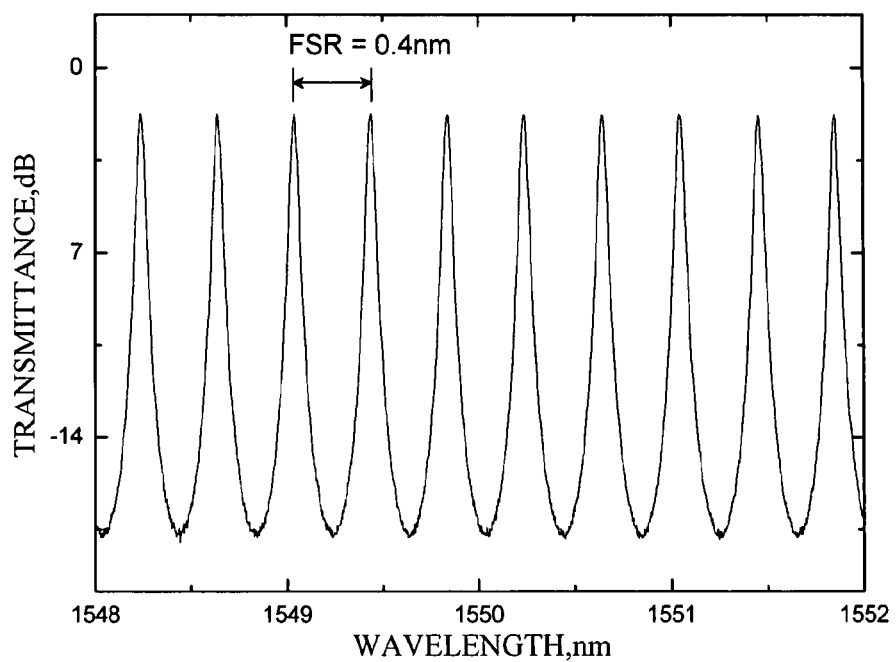
FIG. 4 shows transmission characteristics of the Fabry-Perot filter.
Figure 17A:
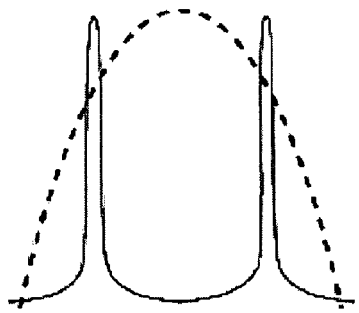
FIG. 17 shows diagrams for explaining the relationship between the reflection wavelength band of the FBG and the FSR of the Fabry-Perot filter.
Figure 17B:
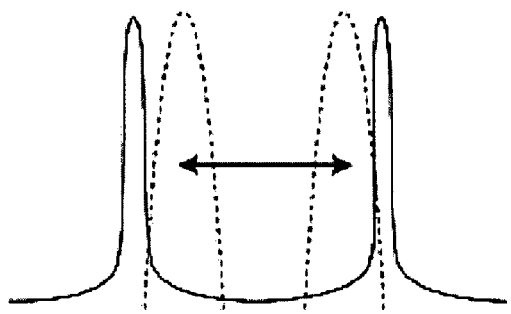
Figure 17C:
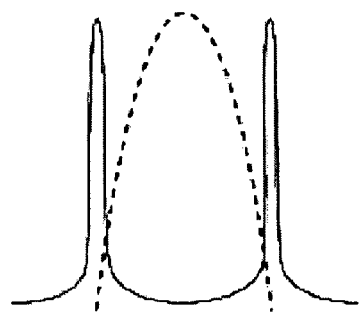

FIG. 3 shows optical characteristics of the FBG 12 and the Fabry-Perot filter 14. Herein, since the FBG 12 has been subjected to an apodization process, the reflection characteristics thereof show no side lobes and the reflection wavelength band thereof is made 0.34 nm, as shown in the figure. Further, regarding the optical characteristics of the Fabry-Perot filter 14, the filter has a FSR of 0.4 nm, which is slightly broader than the reflection wavelength band of the optical characteristics of the FBG 12, and the full width at half maximum transmission is 40 pm. As shown in FIG. 4, the transmission characteristics of the Fabry-Perot filter 14 are characterized in that the transmission region thereof periodically appears for each FSR (Free Spectral Range) frequency. Note that it would be ideal if the reflection wavelength band of the FBG 12 and the FSR of the Fabry-Perot filter 14 were equal to each other. However, as long as the FSR is equal to or greater than the reflection wavelength band, the combination of the FBG 12 and the Fabry-Perot filter 14 functions as a sensor. Namely, as shown in FIG. 17, when the reflection wavelength band>the FSR (FIG. 17(a)), two or more filter transmission regions exist in the reflection wavelength band of the FBG 12. Under such condition, an output from the filter will be a response signal that does not correspond to the waveform of the ultrasound or AE signal received by the FBG 12. Thus, in this case, the combination of the FBG 12 and the filter 14 does not function as a sensor. In contrast, when the reflection wavelength≦the FSR (FIGS. 17(b) and (c)), the filter outputs a response signal equal to the waveform of the ultrasound or AE signal received by the FBG 12, and thus the combination of the FBG 12 and the filter 14 functions as a sensor. Namely, when the reflection wavelength band<the FSR (FIG. 17(b)), the dead zone (the region in which sensor sensitivity is low) of the sensor output expands. In FIG. 17(b), when the reflection wavelength of the FBG 12 falls within the range indicated by the arrow, the sensor sensitivity is low, and when the reflection wavelength band=the FSR shown in FIG. 17(c), the dead zone of the sensor output is caused to be minimized.

Figure 5:
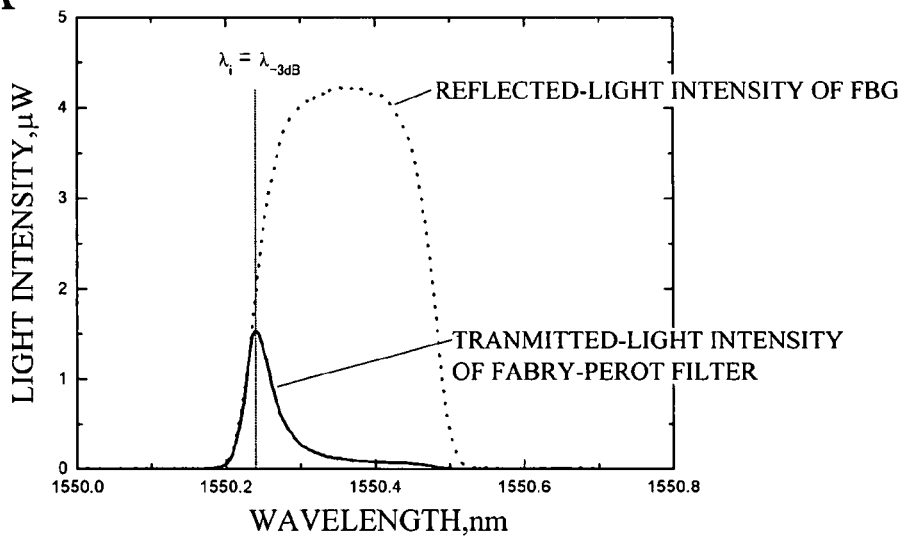
FIG. 5 shows the relationship between the reflected-light intensity of the FBG and the transmitted-light intensity of the Fabry-Perot filter.
Figure 5:
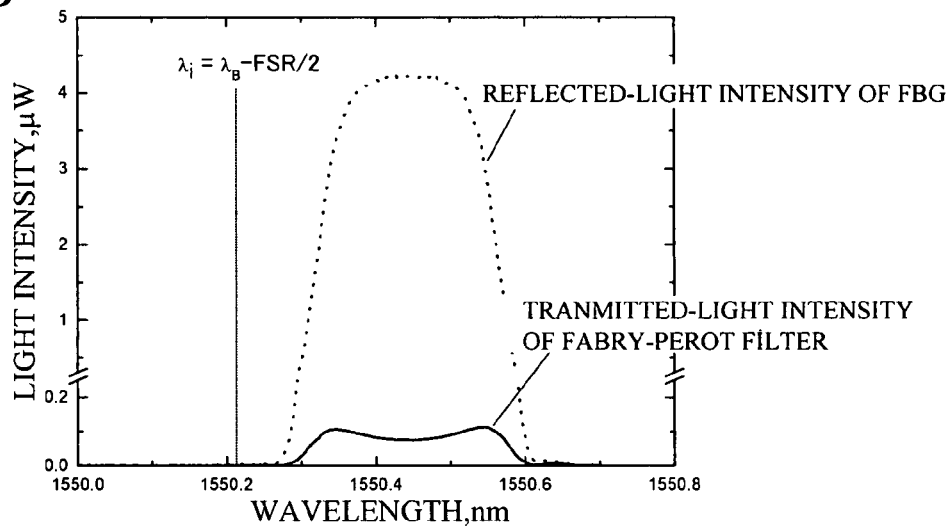
Figure 5:
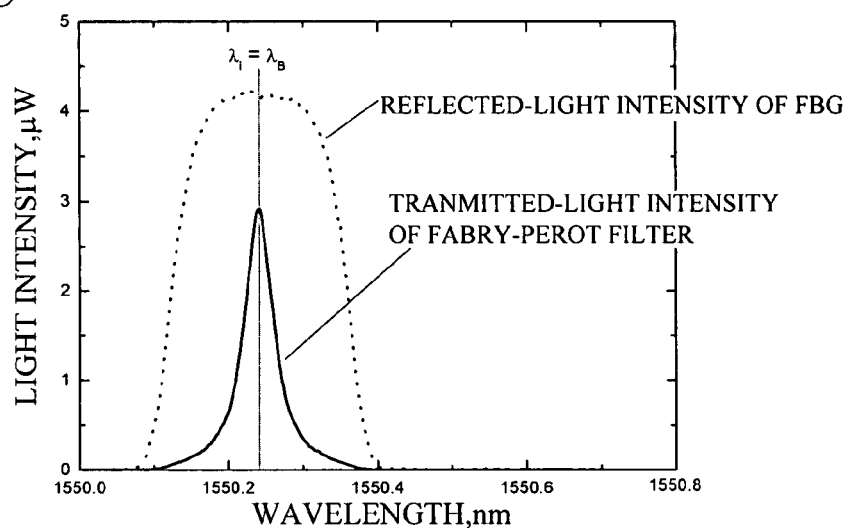

Next, referring to FIG. 5, the influence of the relationship between the Bragg wavelength of the FBG 12 and the transmittance peak wavelength of the Fabry-Perot filter 14 on the sensitivity of ultrasound detection will be described. In FIG. 2, the uniaxial displacement stage 18 is moved so that the FBG 12 is provided with strain, and the Bragg wavelength is changed, so as to detect the ultrasound propagated through the optical fiber from the ultrasound oscillator 17. Herein, three states; that is, a state in which filter-transmittance peak wavelength $\lambda_i$ matches wavelength $\lambda_{-3dB}$ at which the reflectance of the FBG is decreased by half (FIG. 5(a)), a state in which the Bragg wavelength of the FBG is located in the middle of adjacent filter-transmittance peak wavelengths (FIG. 5(b)), and a state in which the filter-transmittance peak wavelength $\lambda_i$ matches the Bragg wavelength $\lambda_B$ of the FBG (FIG. 5(c)), are created, and the ultrasound generated by the ultrasound oscillator is detected by the FBG 12.

Figure 6:
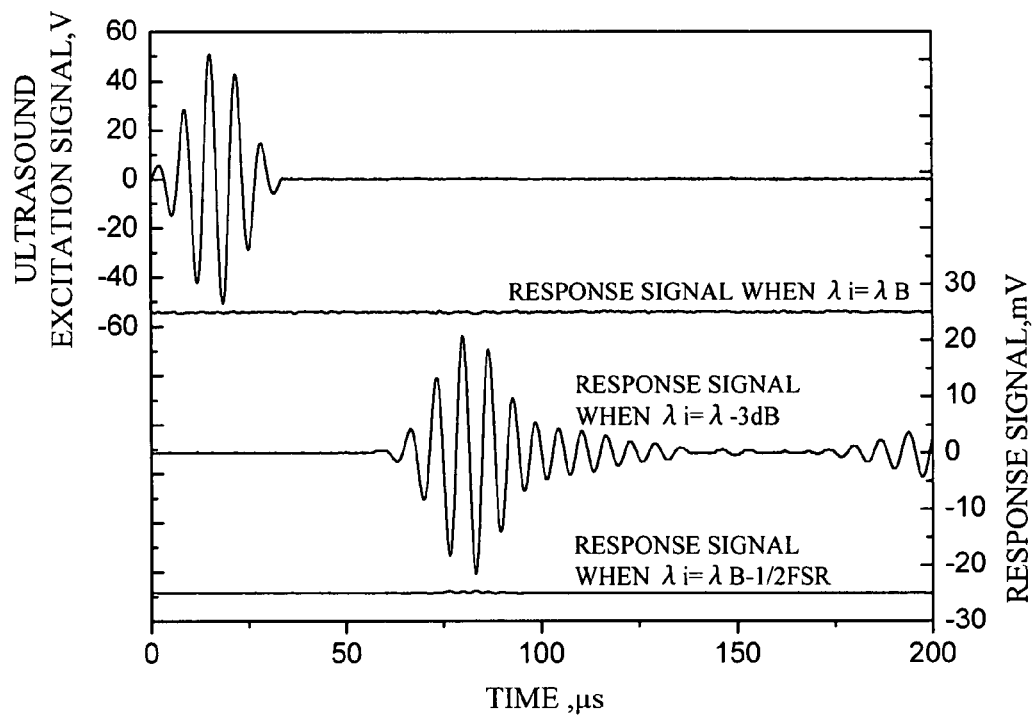
FIG. 6 shows ultrasound response signals when the relationship between the Bragg wavelength of the FBG and the filter-transmittance peak wavelength is changed.

FIG. 6 shows the individual response signals in the above three states and it also shows an excitation signal inputted to the ultrasound oscillator. Namely, in FIG. 6, the photoelectric converter 15 converts the filter-transmitted-light intensity corresponding to the area surrounded by the Fabry-Perot filter transmitted-light intensity curve in FIG. 5(a) to (c) into a voltage signal, and the signal intensity corresponds to the ultrasound (elastic wave) detected by the FBG 12. It is seen from FIG. 6 that, when the filter-transmittance peak wavelength $\lambda_i$ is located at the wavelength $\lambda_{-3dB}$ at which the reflectance of the FBG 12 is decreased by half, the ultrasound is detected with high sensitivity. Since the gradient of the change of the relationship between the reflectance and the wavelength is large and the filter-transmitted-light intensity is sufficient at the wavelength at which the reflectance of the FBG 12 is decreased by half, the ultrasound can be detected with high sensitivity. However, such ultrasound is hardly detected under the other two conditions; that is, the case in which the Bragg wavelength of the FBG 12 is located in the middle of the adjacent filter-transmittance peak wavelengths and the case in which the filter transmittance peak $\lambda_i$ matches the Bragg wavelength $\lambda_B$ of the FBG 12. This is because, in the case of FIGS. 5(b) and (c), there is almost no change in the integration value (area) of the Fabry-Perot filter transmitted-light intensity even when the intensity distribution of the light reflected from the FBG is somewhat displaced due to ultrasound.

Considering the present embodiment more specifically, when the Bragg wavelength of the FBG 12 is located in the middle of the adjacent filter-transmittance peak wavelengths, as can be seen from FIG. 3, there is caused almost no filter transmitted-light intensity associated with a change in the Bragg wavelength of the FBG 12. For example, when the FBG 12 receives tension and the reflection characteristics are caused to shift toward the longer wavelength side, while the transmitted-light intensity in a transmission region existing on the longer wavelength side is increased, the transmitted-light intensity in a transmission region existing on the shorter wavelength side is decreased. Namely, changes of the transmitted-light intensities in the adjacent filter transmission regions cancel each other out. Further, when the filter transmittance peak $\lambda_i$ and the Bragg wavelength $\lambda_B$ of the FBG 12 match with each other, the gradient of the change of the relationship between the reflectance and the wavelength near the Bragg wavelength is small. Thus, even when the Bragg wavelength fluctuates, a change in the filter transmitted-light intensity is small. For these reasons, under the above two conditions, the sensitivity of AE/ultrasound detection is decreased. However, it is assumed that the AE/ultrasound can be detected under conditions other than those two conditions, while the sensitivity varies depending on the positional relationship between the Bragg wavelength and the filter-transmittance peak wavelength.

Second Embodiment

Figure 7:
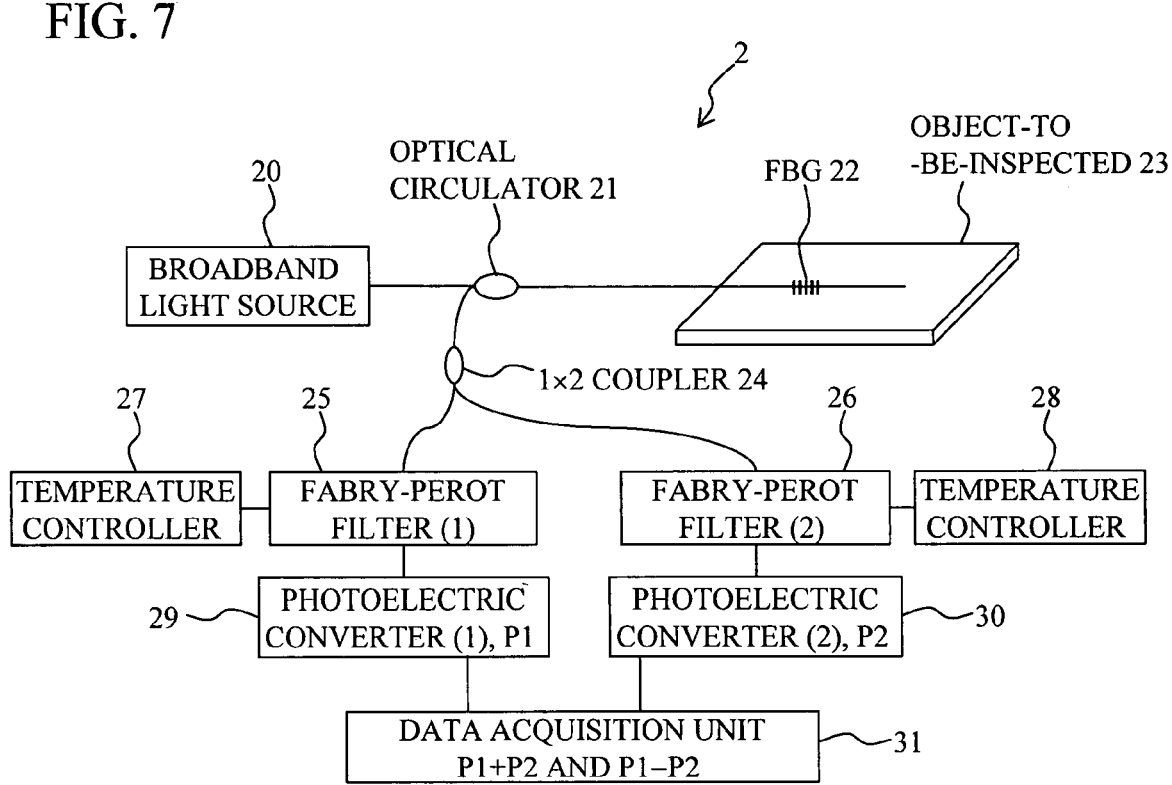
FIG. 7 schematically shows the structure of an AE/ultrasound detection system according to a second embodiment of the present invention.

FIG. 7 shows a basic structure of an AE/ultrasound detection system 2 according to a second embodiment. In the AE/ultrasound detection system 2 of the second embodiment, a broadband light source 20 and two Fabry-Perot filters 25 and 26 are combined.

As shown in FIG. 7, the AE/ultrasound detection system 2 is used for evaluating the soundness of an object-to-be-inspected 23, and it comprises: the broadband light source 20; an optical circulator 21; an FBG 22 (having been subjected to an apodization process); a Fabry-Perot filter (1) 25; a Fabry-Perot filter (2) 26; temperature controllers 27 and 28; a photoelectric converter (1) 29; a photoelectric converter (2) 30; and a data acquisition unit 31.

Figure 9:
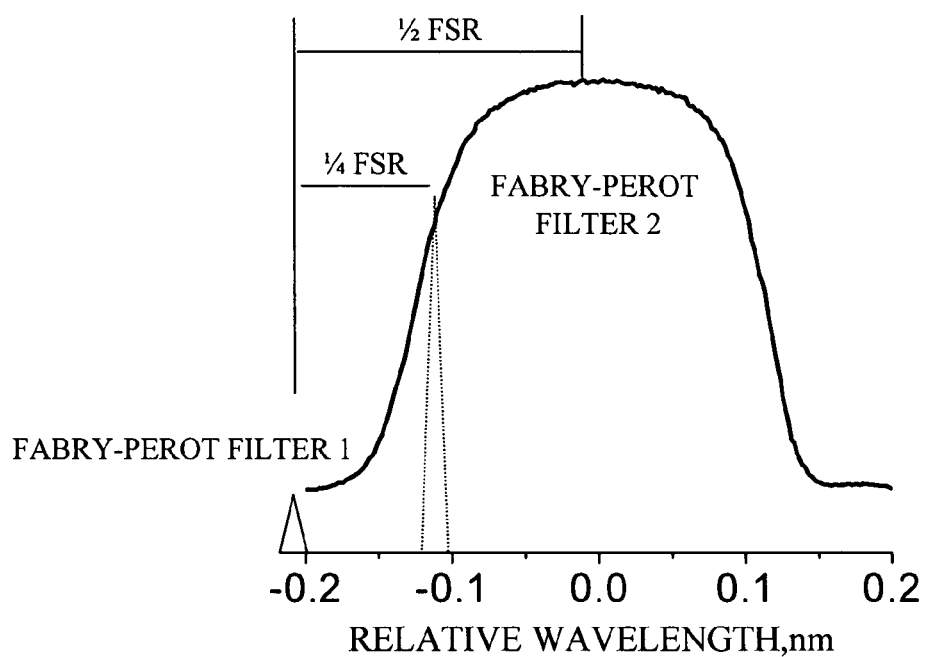
FIG. 9 shows the relationship between the transmittance peak wavelengths of two Fabry-Perot filters and the relationship between such relationship and the reflectance of the FBG.

In FIG. 7, broadband light from the broadband light source 20 enters the FBG 22 via the optical circulator 21. The reflected light from the FBG 22 enters the two Fabry-Perot filters 25 and 26 via the optical circulator 21 and a 1×2 coupler 24. The FBG 22, and the Fabry-Perot filters 25 and 26 used herein are the same as those used in the first embodiment, and as shown in FIG. 9, the temperature controllers 27 and 28 attached to the Fabry-Perot filter (1) 25 and the Fabry-Perot filter (2) 26 make adjustments so that the transmittance peak wavelengths of the two Fabry-Perot filters are separated by FSR/4. While the transmission wavelengths of the Fabry-Perot filters 25 and 26 vary upon receiving the influence of temperature, commercially available Fabry-Perot filters are adapted so that the transmittance wavelengths thereof can be controlled by temperature controllers. Further, by maintaining the temperatures of the Fabry-Perot filters 25 and 26 to be constant with the use of the temperature controllers 27 and 28, it becomes possible to maintain the filter-transmittance peak wavelengths to be constant. The transmitted light from the Fabry-Perot filters 25 and 26 is supplied to the photoelectric converters 29 and 30, respectively. In the photoelectric converters 29 and 30, the light is converted into an electrical output corresponding to the transmitted-light intensity. The data acquisition unit 31 causes a display unit not shown in the figure to display or a recording device not shown in the figure to record the electrical output, as the AE/ultrasound detected by the FBG 22.

Figure 8:
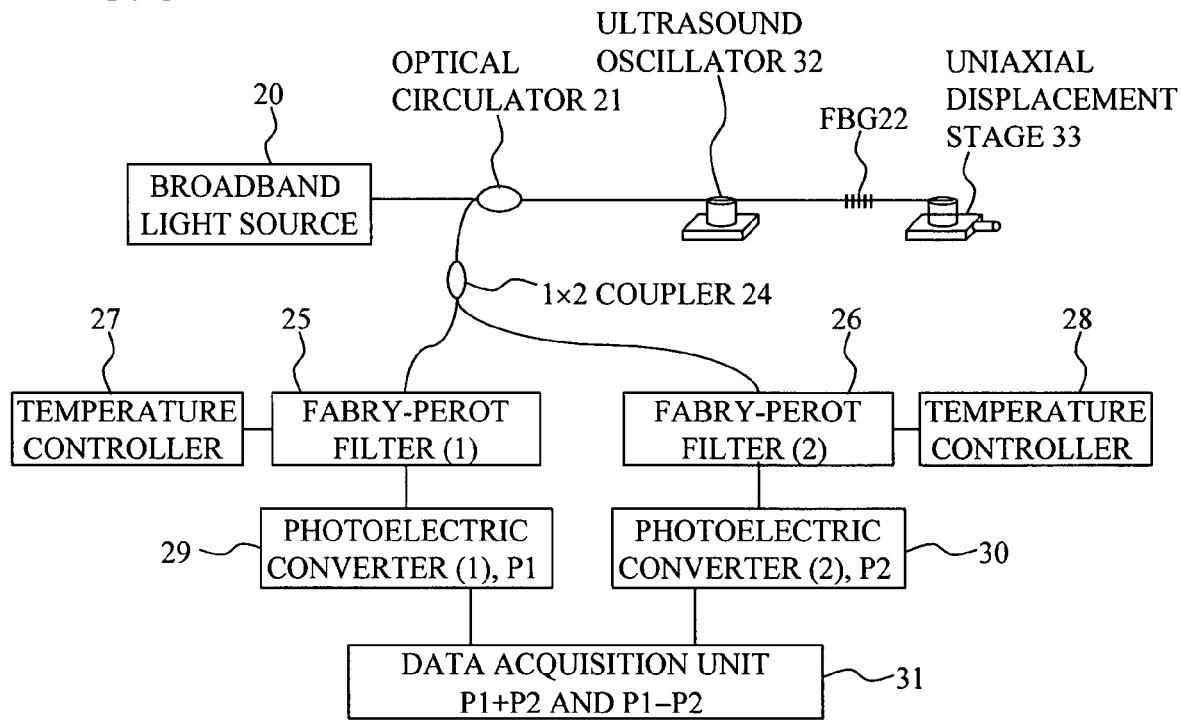
FIG. 8 schematically shows a system used in AE/ultrasound measurement experiment (2).

Next, an AE/ultrasound measurement experiment will be described so that the operation of the AE/ultrasound detection system 2 of the present embodiment will be understood more clearly. FIG. 8 shows a system for the experiment, and an ultrasound oscillator 32 and a uniaxial displacement stage 33 are provided in order to represent a pseudo strain placed on the object-to-be-inspected when conducting the experiment. The other features are the same as those of FIG. 7. Namely, a portion of the optical fiber is attached to the ultrasound oscillator 32, a portion between the FBG 22 and the end of the optical fiber is attached to the uniaxial displacement stage 33, and the uniaxial displacement stage 33 is moved, so as to cause a strain to the object-to-be-inspected 23.

Figure 10:
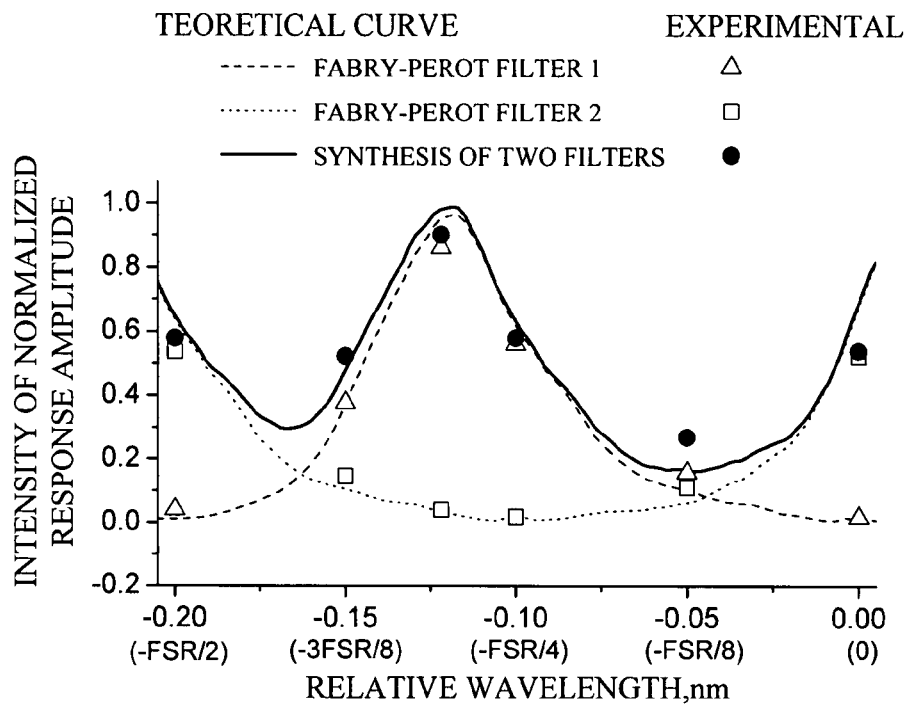
FIG. 10 shows the influence on the intensity of a response amplitude due to the difference between the transmittance peak wavelength of a Fabry-Perot filter (1) 25 and the Bragg wavelength.

In this experiment, the system shown in FIG. 8 is used for the experiment, and in order to examine the influence of the relationship between the Bragg wavelength of the FBG 22 and the transmission peak wavelength of the Fabry-Perot filter on the sensitivity of ultrasound detection, the FBG 22 is provided with a strain, the Bragg wavelength is changed, and the ultrasound is then detected. As shown in FIG. 9, the Bragg wavelength of the FBG is fluctuated so that a relative wavelength between the Bragg wavelength of the FBG and the transmittance peak wavelength of the Fabry-Perot filter (1) falls within the range from −FSR/2 to 0. FIG. 10 shows the intensity of the amplitude of the ultrasound response measured based on the intensity of the transmitted light from each of the Fabry-Perot filter (1) 25 and the Fabry-Perot filter (2) 26, when the Bragg wavelength of the FBG 22 is fluctuated. Further, the sensitivity of the ultrasound response is represented as Expression (1) in view of the relationship between reflectance R and wavelength $\lambda$ of the FBG.

Mathematical Expression 1

$$\text{Sensitivity} = \sqrt{\left(\frac{dR}{d\lambda}\right)^2} \quad (1)$$

Note that FIG. 10 also shows theoretical sensitivity curves that can be expected based on Expression (1).

Figure 11:
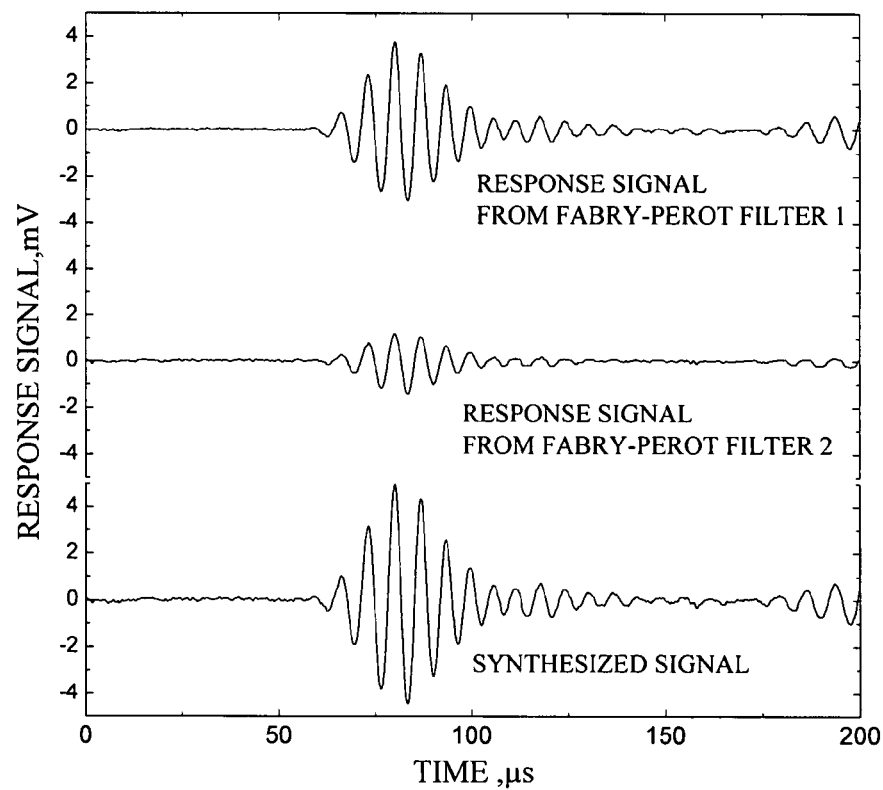
FIG. 11 shows response waveforms and a synthesized signal detected when a relative wavelength is −0.15 mm (−3FSR/8).

The response intensity obtained from the experiment using the Fabry-Perot filter (1) 25 and the Fabry-Perot filter (2) 26 corresponds to the tendency expected based on the theory very well. Further, a large response amplitude can be obtained through synthesis processing that adds and subtracts outputs from both of the filters. For example, when the relative wavelength is −3FSR/8 (−0.15 nm), the response outputs from the Fabry-Perot filter (1) 25 and the Fabry-Perot filter (2) 26 are as shown in FIG. 11.

Figure 12:
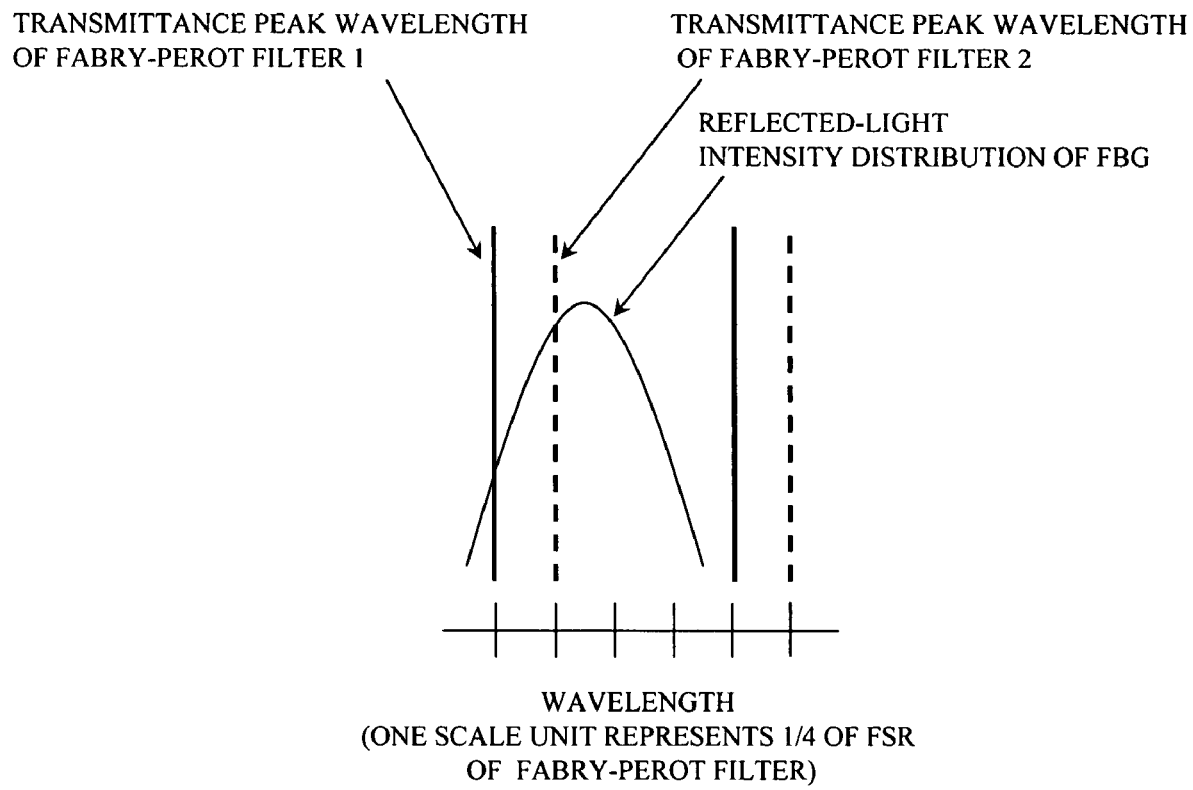
FIG. 12 shows the relationship between the reflected-light intensity of the FBG and the transmittance peak wavelengths of two filters.
Figure 12:
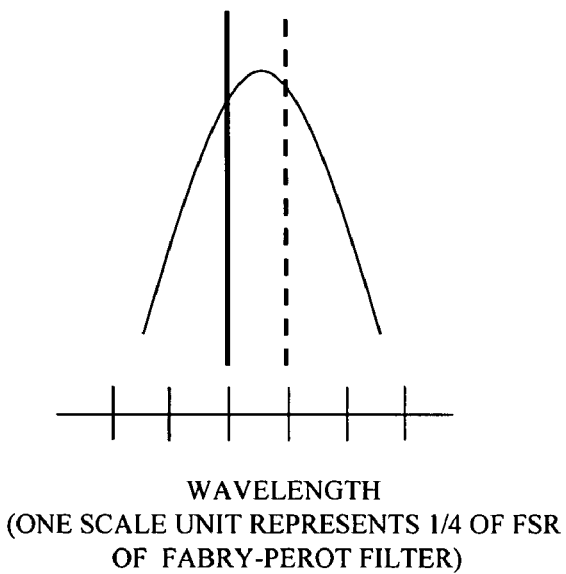

As shown in FIG. 12(a), when the relative wavelength between the Fabry-Perot filter (1) 25 and the Bragg wavelength of the FBG 22 falls in the range of –FSR/2 to –FSR/4, the peak wavelengths of the Fabry-Perot filter (1) 25 and the Fabry-Perot filter (2) 26 exist in the left half of the reflection wavelength region of the FBG, and the response changes depending on the AE/ultrasound from both of the filters are in phase with each other. Thus, a large response signal as shown in FIG. 11 can be obtained by adding an output P1 from the photoelectric converter (1) 29 for measuring the intensity of the transmitted light from the Fabry-Perot filter (1) 25 and an output P2 from the photoelectric converter (2) 30 for measuring the intensity of the transmitted light from the Fabry-Perot filter (2) 26.

Further, when the relative wavelength of the Fabry-Perot filter (1) 25 falls in the range of –FSR/4 to 0, as shown in FIG. 12(b), since the peak wavelengths of the Fabry-Perot filter (1) 25 and the Fabry-Perot filter (2) 26 are separated on the left side and the right side of the Bragg wavelength of the FBG 22, the response changes of both of the filters are in opposite phase with each other. Thus, a large response signal can be obtained by subtracting the output P1 and the output P2.

The data acquisition unit 31 of FIG. 8 performs such addition or subtraction on the outputs P1 and P2 from the photoelectric converter (1) 29 and the photoelectric converter (2) 30, and it allows the displaying/recording of the larger one of the response amplitudes as the AE/ultrasound received by the FBG 22.

<Regarding the FBG Reflection Characteristics>

Figure 13:
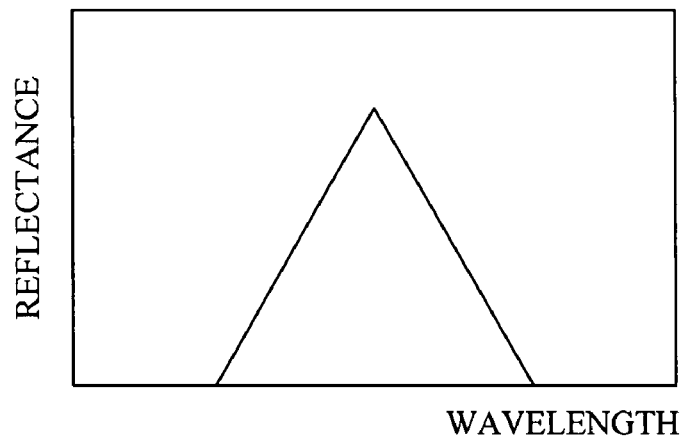
FIG. 13 shows ideal reflection characteristics of the FBG for AE/ultrasound detection.

FIG. 13 shows ideal FBG reflection characteristics for AE/ultrasound detection. It is assumed that, based on the systems according to the above first and second embodiments, if the FBG characteristics exhibited triangular reflection characteristics as shown in FIG. 13, it could be possible to realize constant AE/ultrasonic detection sensitivity, irrespective of the Bragg wavelength of the FBG. However, the creation of a FBG having such triangular reflection characteristics is practically impossible.

Figure 14:
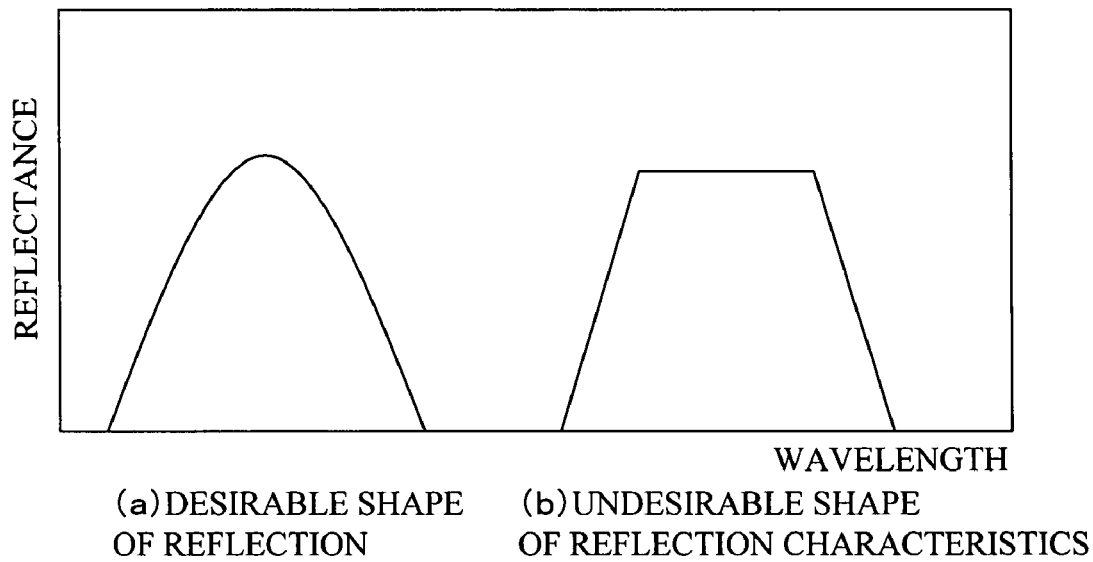
FIG. 14 shows a desirable shape of reflection characteristics and an undesirable shape of reflection characteristics for AE/ultrasound detection.

Consequently, as shown in FIG. 14(a), for AE/ultrasound detection, it is desirable to use an FBG having reflection characteristics in which the reflectance is not saturated even in a wavelength region in which the reflectance reaches maximum. On the other hand, an FBG having such reflectance as shown FIG. 14 (b); that is, the reflectance saturated in a wavelength region in which the reflectance reaches maximum, is not desirable, since in such case, the detection sensitivity may reach zero upon AE/ultrasound detection.

Figure 15:
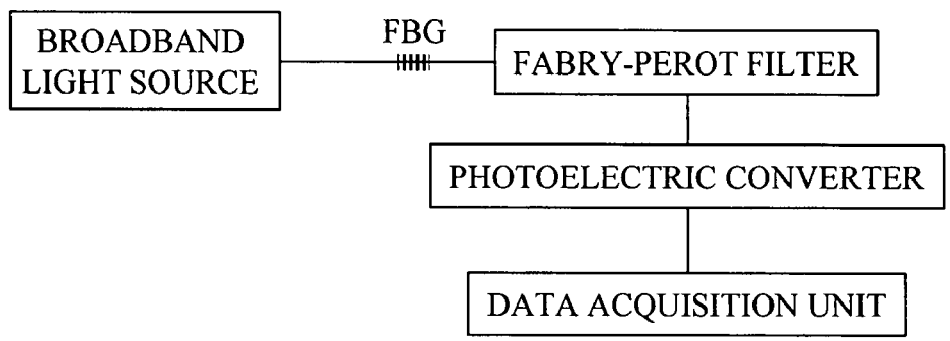
FIG. 15 schematically shows the structure of an AE/ultrasound detection system with the use of the transmitted light from the FBG.

Other Embodiments (1) While in the above first and second embodiments, the reflected light from the FBG is caused to enter the Fabry-Perot filter, it is conceivable that even if the transmitted light from the FBG is caused to enter the Fabry-Perot filter in such manner as shown in FIG. 15, the AE/ultrasound detection is possible under the same conditions.

Figure 16:
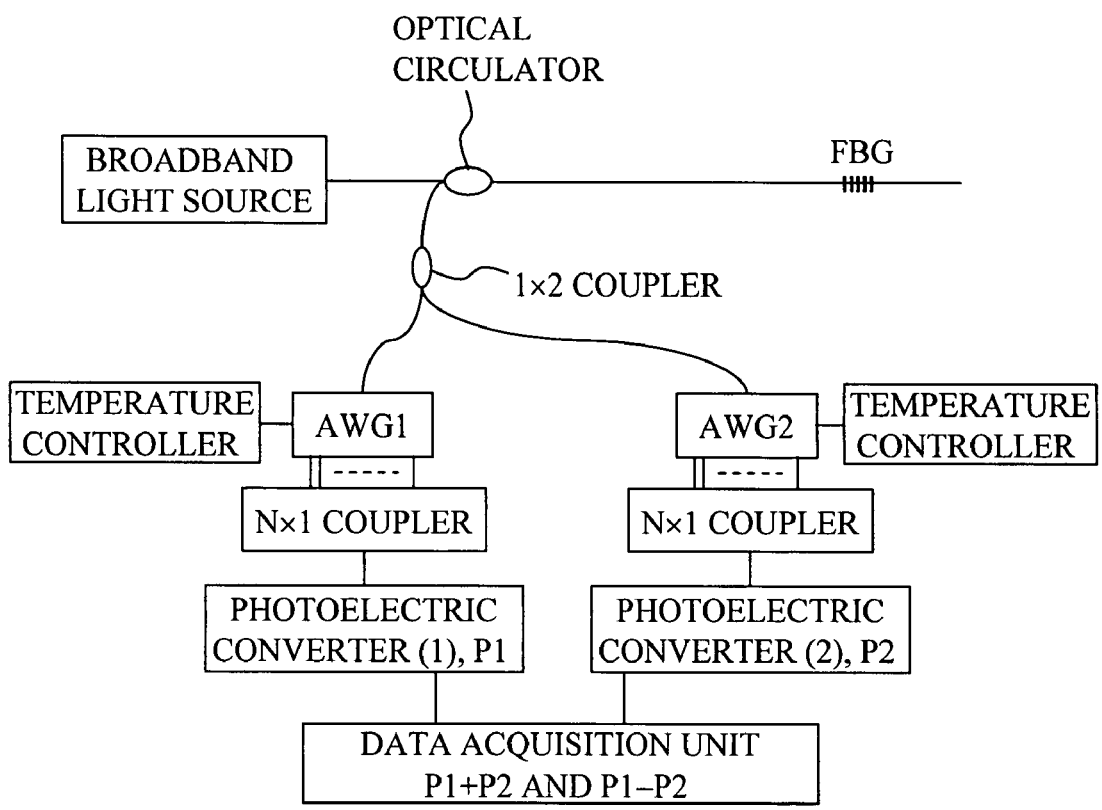
FIG. 16 schematically shows the structure of an AE/ultrasound detection system with the use of AWGs having a number N of output terminals, instead of the Fabry-Perot filter.

(2) While in the above first and second embodiments, a Fabry-Perot filter is used as an optical filter having periodic transmission characteristics, similarly, it is conceivable that, if a system as shown in FIG. 16 is structured with the use of an AWG (Arrayed-Waveguide Grating) having periodic transmission characteristics, the AE/ultrasound detection can be similarly made. In such case, the transmission characteristics of the AWG are made the same as those in the system using the Fabry-Perot filter.

With the use of the AE/ultrasound measuring technique using the FBG as described above, it is conceivable that the soundness of a structure can be monitored by attaching the FBG to a structure-to-be-inspected and then detecting the AE generated upon microscopic material destruction. Alternatively, such technique can be applied for detecting defection using ultrasound, for example.

Effects of the Embodiments

In accordance with one embodiment of the present invention, a broadband-wavelength light is caused to enter the FBG attached to an object-to-be-inspected, part of the reflected light (or the transmitted light) from the FBG is transmitted through a Fabry-Perot filter (or an AWG filter) having periodic transmission characteristics, and the intensity of the light transmitted through the filter is converted into an electric signal. Thus, even when the Bragg wavelength of the FBG is fluctuated due to temperature or strain, the AE/ultrasound received by the FBG can be detected.

Since the Fabry-Perot filter has an FSR equal to or greater than the reflection wavelength band or transmission wavelength band of the FBG, AE/ultrasound detection can be made more reliably.

Further, since the filter-transmission peak wavelength is controlled (with the use of a temperature controller) so that it is equal to the wavelength at which the reflectance or transmittance of the FBG is decreased by half, the AE/ultrasound can be detected with high sensitivity.

In accordance with another embodiment of the present invention, broadband wavelength light is caused to enter the FGB attached to an object-to-be-inspected, the reflected light (or the transmitted light) from the FBG sensor is divided so as to produce two kinds of reflected light, part of the reflected light is transmitted through Fabry-Perot filters having periodic transmission characteristics (AWG filters may alternatively be used. The transmittance peak wavelengths of the two filters are separated from each other by FSR/4), and the intensity of the transmitted light from each of the two filters is converted into an electrical signal. Thus, even when the Bragg wavelength of the FBG is fluctuated due to temperature and strain, the AE/ultrasound received by the FBG can be detected. Further, since the electrical signal corresponding to the intensity of the transmitted light from each of the filters is subjected to addition and subtraction processes, even when response changes depending on the AE/ultrasound are in phase or opposite phase with each other, a large response signal can be reliably obtained, and therefore, AE/ultrasound detection can be made reliably.

While embodiments of the present invention have been described above, the present invention is not limited thereto. Needless to say, any structural modification, addition, or substitution is possible, without departing from the essential scope of the present invention.

What is claimed is:

1. An AE/ultrasound detection system comprising:
a broadband light source for emitting broadband-wavelength light;
an FBG sensor that is attached to an object-to-be-inspected and that the broadband-wavelength light enters;
light dividing means that divides the reflected light or transmitted light from the FBG sensor so as to produce a first reflected light or transmitted light and a second reflected light or transmitted light;
a first filter having periodic transmission characteristics for transmitting part of the first reflected light or transmitted light;
a second filter having periodic transmission characteristics and having the transmittance peak wavelength separated from that of the first filter by FSR/4, for transmitting part of the second reflected light or transmitted light wherein FSR, Free Spectral Range, refers to the spacing in optical wavelength between two successive reflected or transmitted optical intensity maxima or minima of an interferometer or diffractive optical element; and photoelectric conversion means for converting the intensity of the transmitted light from each of the first and second filters into an electric signal.

2. The AE/ultrasound detection system according to claim 1, further comprising processing means for performing addition and subtraction processes on the electric signal that is obtained by the conversion means and that corresponds to the intensity of the transmitted light from each of the filters.

3. The AE/ultrasound detection system according to claim 1, wherein the broadband light source emits broadband light including the Bragg wavelength of the FBG sensor, and the first and second filters have an FSR equal to or greater than the reflection wavelength band or transmission wavelength band of the FBG.

4. The AE/ultrasound detection system according to claim 1, wherein the FBG sensor is an apodization-processed FBG whose reflected-light or transmitted-light characteristics have no side lobes, and wherein the characteristics are not saturated in a wavelength region in which the reflectance reaches maximum.

5. The AE/ultrasound detection system according to claim 1, wherein the first and second filter are Fabry-Perot filters.

6. The AE/ultrasound detection system according to claim 1, wherein the first and second filter are AWG filters.

7. A material monitoring apparatus comprising the AE/ultrasound detection system according to claim 1 for finding microscopic material destruction by detecting acoustic emission generated upon material destruction; and an output device configured to output information of the microscopic material destruction which has been found by the AE/ultrasound detection system.

8. A nondestructive inspection apparatus comprising the AE/ultrasound detection system according to claim 1 for conducting nondestructive inspection on a material or a structure with the use of ultrasound; and an output device configured to output the inspection result of the AE/ultrasound detection system.

* * * * *